United States Patent [19]

Avoy

[11] 4,259,952

[45] Apr. 7, 1981

[54] BLOOD DILUTING METHOD AND APPARATUS

[76] Inventor: Donald R. Avoy, 8 Hollywood Ave., Los Gatos, Calif. 95030

[21] Appl. No.: 918,279

[22] Filed: Jun. 22, 1978

[51] Int. Cl.[3] .............................................. A61M 5/00

[52] U.S. Cl. ................................ 128/214 D; 128/272; 128/272.3

[58] Field of Search ............... 128/214 D, 214 R, 272, 128/272.3, 214 C

[56] References Cited

U.S. PATENT DOCUMENTS

| | | | |
|---|---|---|---|
| 3,023,750 | 3/1962 | Baron | 128/214 F |
| 3,064,647 | 11/1962 | Earl | 128/272 X |
| 3,187,750 | 6/1965 | Tenczar, Jr. | 128/214 D X |
| 3,461,868 | 8/1969 | Palich | 128/214 D |
| 3,547,401 | 12/1970 | Beall et al. | 128/214 D X |
| 3,685,795 | 8/1972 | Caster | 128/214 D |
| 3,756,237 | 9/1973 | Chittenden et al. | 128/227 |
| 3,788,369 | 1/1974 | Killinger | 128/272.3 X |
| 3,896,733 | 7/1975 | Rosenberg | 128/214 R |
| 3,945,380 | 3/1976 | Dabney et al. | 128/214 D |
| 4,038,983 | 8/1977 | Mittleman et al. | 128/214 C |

FOREIGN PATENT DOCUMENTS

| | | | |
|---|---|---|---|
| 2356905 | 6/1974 | Fed. Rep. of Germany | 128/214 D |

*Primary Examiner*—Henry K. Artis

[57] ABSTRACT

An apparatus for diluting packed red blood cells contained in a transfusion bag is provided comprising a flexible, squeezable diluent bag for containing a diluent for diluting the red blood cells in the transfusion bag. A tubular assembly with one or more fittings is provided for permanently attaching the diluent bag to an input port of the transfusion bag. The fittings are adapted for preventing a non-destructive, non-removable separation of the two bags. A uni-directional flow fluid valve means is provided for preventing reverse fluid flow from the transfusion bag to the diluent bag.

8 Claims, 4 Drawing Figures

BLOOD DILUTING METHOD AND APPARATUS

BACKGROUND OF THE INVENTION

The present invention relates to methods and apparatus for collecting, processing and transfusing blood in general and, in particular, to a novel method and apparatus for diluting packed red blood cells contained in a transfusion bag.

Transfusion bags containing packed red blood cells are obtained in the first step of conventional blood processing in which whole blood obtained from a donor is separated into its component parts.

A principal physical characteristic of packed red blood cells which gives rise to the present invention and which is evident during normal transfusions is their high viscosity and corresponding relatively low flow rate in comparison to the flow rate obtained with whole blood.

Whether the low flow rate in a normal transfusion of packed red blood cells is acceptable depends on the nature or character of the therapeutic application or procedure involved. In cases of emergency injuries and operations involving trauma and high volume blood loss, low flow rates are generally unacceptable. In these cases, the packed red blood cells must be diluted or whole blood must be used.

At the present time, using conventional methods and apparatus, the dilution of packed red blood cells is time-consuming and troublesome. Quite frequently, it is wasteful of diluent used for diluting the packed red blood cells. It may also be dangerous to a patient if the diluent used is incorrect in amount or type, as may occur in the excitement of an emergency or operation involving high volume blood loss.

On the other hand, the use of whole blood simply to avoid the time and trouble of diluting packed red blood cells, when only the extra oxygen-carrying capacity of the red blood cells is required, has long been recognized by medical authorities as being wasteful of the non-required blood components. The use of whole blood when it is necessary only for high flow rates is also recognized as being potentially dangerous to a patient, as will be further explained below.

The time and trouble encountered by a physician and the potential danger to a patient and loss of supplies using conventional methods and apparatus for diluting packed red blood cells may be made more clear by means of a simple and brief description of conventional blood collecting, processing and transfusing techniques and apparatus.

Conventionally, whole blood is received from a donor in a relatively small plastic bag having a volume of about 500 cc. In preparation for receiving the whole blood, the bag, commonly called a primary bag, is filled with a small quantity of an anti-coagulent.

Coupled to the primary bag by means of a plurality of hollow tubes, there is provided a number of satellite bags. The primary and satellite bags are interconnected by the tubes in such a manner that no air is admitted to the bags and the component parts of the blood in the course of the blood processing can be transferred from one bag to another with no potential hazard from bacterial contamination. This was not possible in the past when blood was collected, processed and transfused using glass bottles.

In the past, any penetration of the blood containers, as by a needle or the like inserted through the rubber stoppers used for closing the bottles created the potential hazard of bacterial contamination. This resulted in a requirement that the potentially contaminated blood components be used within twenty-four hours. The twenty-four hour restriction insured that a patient's normal biological immunities could handle the bacterial contamination if it occurred.

In the first step of the processing of whole blood into its component parts, a primary bag filled with whole blood and its satellites are placed in a centrifuge. After a predetermined time at a predetermined RPM, the red blood cells and plasma in the whole blood are separated. Thereafter, about 200 cc of the plasma is transferred from the primary bag to a first one of the satellite bags. The other satellite bags are used for the subsequent separation of additional blood components from the plasma, but forming no part of the present invention, the steps involved need not be further explained for an understanding of the present invention. It need only to be understood that the other components are very important for blood component therapy and can be obtained only from existing quantities of whole blood.

After the removal of the 200 cc of plasma from the primary bag, the primary bag is sealed, as by thermal bonding techniques, and separated from the satellite bags for storage in a refrigerator until the red blood cells contained therein are required for a transfusion. At this point, and for obvious reasons, most persons handling the primary bag now call it a transfusion bag. With the plasma removed, the red blood cells are much closer together and, being without their normal supporting medium, plasma, become "packed," hence the designation, packed red blood cells.

Having considered how the packed red blood cells are obtained, consideration may now be given to how they are diluted using conventional methods and apparatus.

When a physician orders packed red blood cells for a transfusion and there is a possibility that a high-volume, high-flow-rate transfusion may be required, an appropriate diluent will normally also be ordered. The orders are generally directed to a local in-house blood service. Alternatively, the blood service may provide the red blood cells while the diluent is obtained from a supply of various types of diluents stored close at hand. This is possible since typical diluents are simply isotonic or slightly hypotonic saline solutions and do not require special storage facilities. Regardless of the source of the diluent, most facilities heretofore stored and supplied the diluent in large, 500–1000 cc glass bottles.

In practice, if the diluting of packed red blood cells is required, a physician typically suspends the diluent bottle from a first rack or hanger and a unit or transfusion bag of packed red blood from another rack or hanger. A tube is then inserted in the diluent bottle and in a port of the transfusion bag. Generally the tube is provided with a needle or the like at one or both of its ends as a fitting to effect the coupling. To prevent reverse flow from the transfusion bag to the diluent bag, the transfusion bag is usually maintained at a position below the diluent bottle.

As may be recalled from the foregoing discussion, the amount of plasma removed from the transfusion bag is typically 200 cc. Accordingly, in the course of diluting the packed red blood cells, it is necessary for the physician to carefully control the amount of diluent used to return the packed red blood cells to the concentration present in whole blood. Since the gravity flow is not usually very turbulent, it is also frequently necessary for the physician or an attendant to agitate the transfusion bag to mix the packed red blood cells and diluent homogeneously.

In many non-emergency cases and in particular in the case of an emergency or an operation involving high-volume blood loss, it can be seen that the time it takes to dilute a transfusion bag, the care that must be exercised to insure that only the proper amount of diluent is added to the bag and the trouble that is involved in having to agitate the bag all tend to make the diluting of packed red blood cells, using conventional methods and diluent bottles, unacceptable. It should also be noted that, unless all of the diluent is used once a diluent bottle has been penetrated, the remaining diluent must be discarded. This is because, as previously discussed, any penetration of a blood or diluent container creates a potential hazard for bacterial contamination requiring that the components and diluent be used immediately.

Another problem with conventional diluting methods and apparatus is that the availability of various types of diluents in the same type of container can give rise, and has not infrequently given rise, in the excitement of an emergency or the like, to the inadvertent use of the wrong diluent.

For the foregoing reasons, and becasue the attending physician is the person who is ultimately responsible for the proper dilution and administration of the blood, blood service personnel and others not under the direct supervision of the physician are not in a position to relieve the physician of the time and trouble associated with the use of conventional methods and apparatus for diluting packed red blood cells.

Turning now to the use of whole blood as a substitute for diluting packed red blood cells, as previously discussed, it has long been recognized as wasteful and potentially dangerous in many, if not a majority of cases. For example, in Volume 212, No. 1 of the *Journal of the American Medical Association,* dated Apr. 6, 1970, in an article entitled "Whole Blood Use Called Wasteful," it is contended that "component transfusion therapy is better transfusion therapy," and, referring to a then new handbook, it is stated: "The use of whole blood is 'shotgun' therapy, wasting valuable components and endangering the patient with the unnecessary burdens of volume, acidosis, electrolytes and antibodies." In the same article, a past president of the American Association of Blood Banks is reported as stating: "Acute blood loss resulting from surgery or trauma is about the only remaining case in which using whole blood remains preferable to components."

In the same article it is stated: "Transfusion of red blood cells (also referred to as concentrated, packed, or enriched red blood cells) rather than whole blood, is generally the best and safest method of fulfilling a patient's need for increased oxygen-carrying capacity. Whether that need results from chronic anemia or acute blood loss, red blood cells, properly prepared, have the same shelf life as whole blood."

In the article, some of the advantages of packed red blood cell transfusions pertinent to the present invention are listed:

(1) The risk from metabolic by-products which accumulate in plasma during storage of whole blood (such as lactic acid, potassium, inorganic phosphate and ammonia) is reduced.

(2) The risk of reactions to allergens and antibodies in plasma is reduced.

(3) The risk of reactions to plasma protein antigens is reduced in multi-transfused recipients.

In summary, the article concludes with the statement that, "it is likely that from 60% to 80% of blood transfusion needs can and should be met by use of red blood cells (rather than whole blood)."

If packed red blood cells were used instead of whole blood, considerably less whole blood would be required to obtain the necessary component parts for specific applications. In spite of this fact, it is reported in the *Lancet,* Letters to the Editor, Feb. 15, 1969, at page 372, that "The high viscosity of packed red blood cells renders their clinical use very difficult."

Even though the problems associated with the use of conventional methods and apparatus for diluting packed red blood cells was well recognized as far back as early 1969, both the problems and the absence of any adequate solution therefor has persisted until the present invention, as evidenced by a recent article in *Transfusion.* In an article entitled "Microaggregate Content and Flow Rates of Packed Red Blood Cells," *Transfusion,* September-October, 1977, pages 484–489, it is reported that: "It is frequently maintained that the flow rate of red blood cells is too slow to be useful during the brisk bleeding that may be encountered at operations."

In addition to the foregoing considerations militating against the use of whole blood as a substitute for properly diluted packed red blood cells, there is the consideration of the amount of whole blood necessary to supply the present needs of both those using blood components and whole blood.

The above quoted estimate of 60–80% of blood optimally being transfused as packed red blood cells is based on their limited use in surgery and trauma for the reasons discussed. If the dilution of packed red blood cells were made convenient and simple, it is likely that virtually all blood transfusions could be achieved using diluted packed red blood cells. This could result in an additional 1,000,000 liters of plasma from whole blood per year in this country, which would substantially reduce or eliminate the need for paid plasma donors.

As the amount of blood and plasma obtained from commercial sources is reduced, the problems associated with hepatitis and other blood-related diseases are likely to also be reduced. Needless to say, the cost of collecting the blood will, of course, be reduced substantially.

SUMMARY OF THE INVENTION

In view of the foregoing, principal objects of the present invention are a method and apparatus for diluting packed red blood cells contained in a transfusion bag which are quick and easy to use, reliable and free of the potential hazards of bacterial contamination associated with prior known conventional methods and apparatus.

In accordance with the above objects of the present invention, there is provided a flexible, squeezable diluent bag having a capacity of about 200 cc. The capacity of the diluent bag corresponds to the volume of blood components removed from the whole blood in the first step of conventional blood processing. Extending from the bag is a hollow tubular assembly comprising a tubular member. Fitted to the free end of the tubular member is a conically-shaped male fitting. The male fitting is adapted to penetrate one of a plurality of ports in a conventional transfusion bag. Typically the port is elastic. As the fitting is fitted into the port, the port expands about the fitting and closes upon it as the head of the fitting passes through and into the transfusion bag. As the fitting passes into the transfusion bag, the port forms a fluid-tight seal therewith, preventing its non-destructive removal from the port. Alternatively, both ends of the tubular member may be fitted with such a fitting for insertion in both the transfusion and the diluent bags.

Between the transfusion bag and the diluent bag, there is provided a uni-directional flow, fluid valve means. The fluid valve means allows fluid to flow from the diluent bag to the transfusion bag, but prevents fluid from flowing in the reverse direction from the transfusion bag to the diluent bag.

In practice a physician ordering blood will receive one or more units of packed red blood cells in a transfusion bag having a plurality of inlet/outlet ports. When the packed red blood cells are received, the physician will ordinarily insert one end of an IV set in one of the inlet/outlet ports with the opposite end being provided with a needle or the like for inserting in a patient. Depending on the physician's needs, an equal number of bags of diluent may also be supplied with the transfusion bags. At the time of their delivery to the physician, the Blood Bank or other service may or may not have inserted the tubing from the diluent bags in one of the inlet/outlet ports of the transfusion bags. Whether this is done depends upon the physician's requirements and orders. In any event, if a diluent and a transfusion bag have been pre-coupled by the blood service, the diluent bag, being permanently and non-removably attached to the transfusion bag is readily available for inspection by the physician, who can determine by visual observation the nature and quantity of the diluent in the diluent bag. If the blood service diluted the packed red blood cells in the transfusion bag before delivery thereof to the physician, the inseparability of the diluent bag from the transfusion bag provides the physician with the information necessary to determine that a proper diluent in quantity and type was used.

If the physician performs the diluting with the diluent bag pre-coupled to the transfusion bags, it is simply necessary for the physician to vigorously squeeze the diluent bag with one hand, causing all of the diluent to pass into the transfusion bag, with the one-way valve member preventing reverse fluid flow therefrom. The size and shape of the bag is chosen to insure single-handed operation. The turbulence generated by the vigorous squeezing of the diluent bag agitates the packed red blood cells, causing a rapid, homogeneous mixture of diluent and packed red blood cells.

As can be seen from the above discussion, because of the controls exercisable in fabricating the diluent bags according to the present invention, the disadvantages of time-consuming and potentially incorrect diluting of packed red blood cells in a transfusion bag are avoided.

DESCRIPTION OF THE DRAWINGS

The above and other objects, features and advantages of the present invention will become apparent from the following detailed description of the accompanying drawings in which.

DETAILED DESCRIPTION

Figure 1:
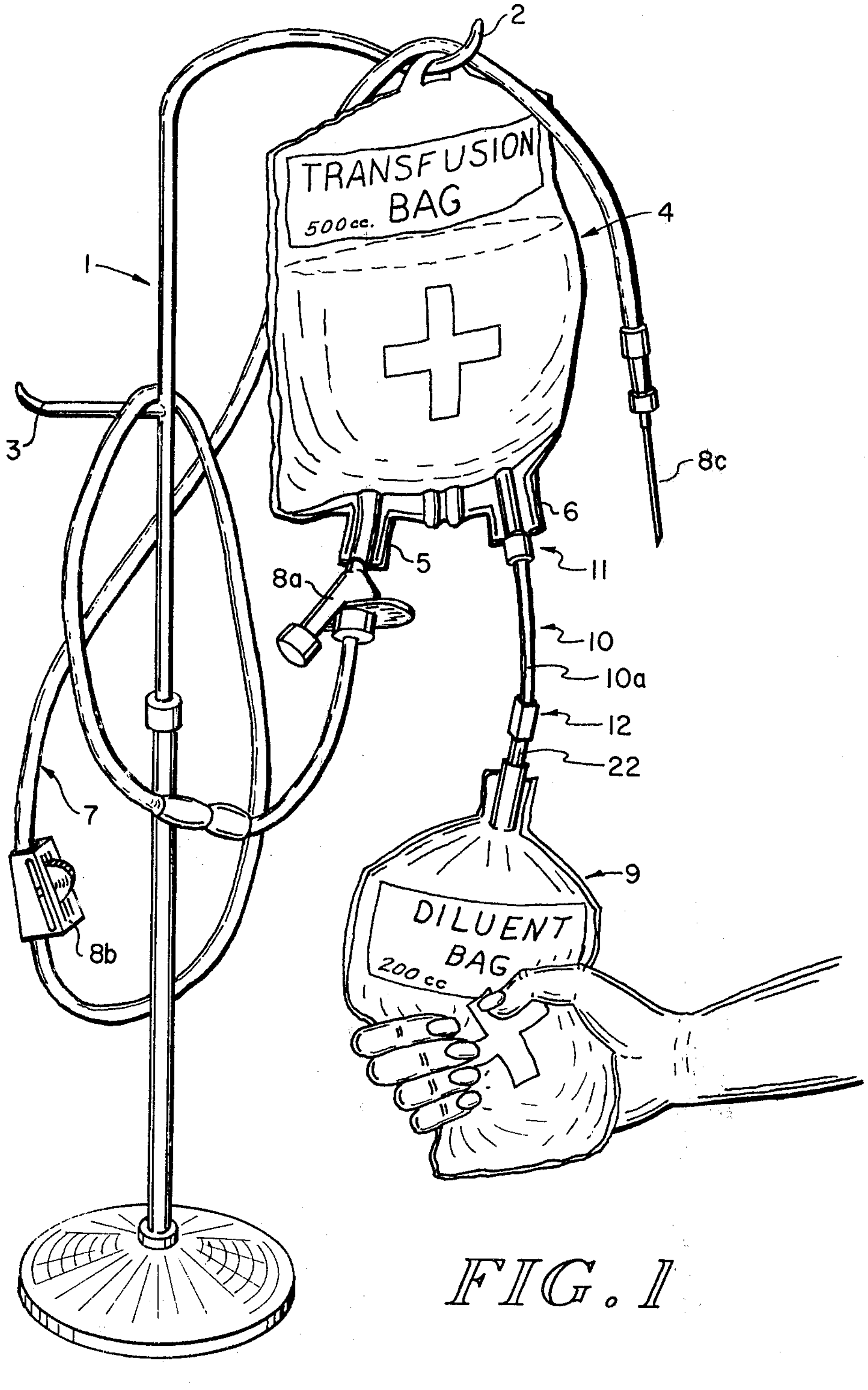
FIG. 1 is a perspective view of a typical transfusion set with a diluent bag according to the present invention pre-coupled to a conventional transfusion bag.

Referring to FIG. 1, there is provided a conventional stanchion 1, comprising a pair of hooked members or hangers 2 and 3. Suspended from the hook 2 is a conventional transfusion bag 4. At the lower end of the transfusion bag 4 there is provided a pair of fitting receiving inlet/outlet ports 5 and 6. Extending from the inlet/outlet port 5 there is provided an IV set 7 fitted with a medication port 8*a*, a flow control valve member 8*b* and a needle 8*c*. The needle 8*c* is provided for insertion in a vein or the like of a patient. Suspended from the inlet/outlet port 6 there is provided, according to the present invention, a diluent bag 9.

Referring to the bag 9, the diluent bag 9 comprises a flexible, squeezable container having a volume of approximately 200 cc. Typically the bag 9 is made of plastic and has a size and shape such that all or most of the contents thereof can be expressed therefrom by a vigorous squeezing of one hand.

Extending from one end of the bag 9 there is provided a tubular assembly 10 comprising a hollow tubular member 10*a*. Fitted to one end of the tubular member 10*a* is a fitting 11. Fitted to the opposite end of the tubular member 10 there is provided a uni-directional flow fluid valve means 12. Coupling the valve means 12 to the diluent bag 9 is a tubular member 22. The opposite end of the member 22 is sealed to the bag 9 in a fluid-tight manner as by thermal bonding techniques.

Figure 2:
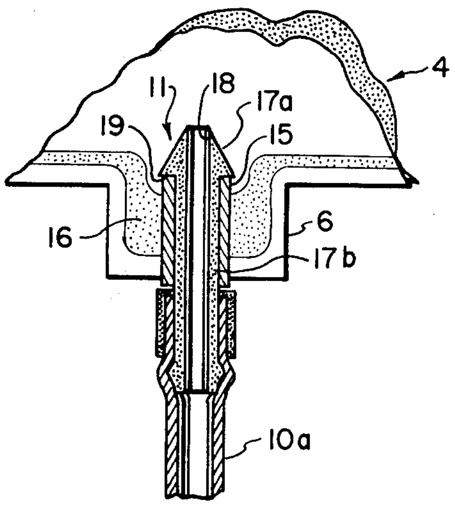
FIG. 2 is a cross-sectional view of a fitting for providing a permanent non-removable coupling according to the present invention.

Referring to FIG. 2, the inlet/outlet port 6 of the transfusion bag 4 is provided with a cylindrical, relatively stiff inner tubular member 15. The tubular member 15 is provided for receiving a fitting and is integrally secured in the bag 4 as by a fluid-tight seal formed by thermal bonding as at 16.

The fitting 11 attached to the end of the tubular member 10*a* is adapted for insertion in the member 15 of port 6 and has a conically-shaped head portion 17*a*, a cylindrical body portion 17*b* and a centrally located fluid passageway 18 extending therethrough. At the base of the conically-shaped head portion 17*a*, there is provided a radially outwardly extending annular shoulder 19.

The tubular member 15 of the inlet/outlet port 6, though relatively stiff, is made of plastic or other flexible material, and is elastic so as to fit snugly around the cylindrical body 17*b* of the fitting 11 below the head portion 17*a*.

In use, as the fitting 11 is forcibly pushed into the member 15 of the inlet/outlet port 6, the member 15 is caused to spread about the head portion 17*a*. As the shoulder portion 19 at the bottom of the head portion 17*a* clears the interior end of the member 15, the fitting 11 is captured by the closing of the member 15 about the cylindrical body portion 17*b*. At this point it is no longer possible to withdraw the fitting 11 from the inlet/outlet port 6 nondestructively. Thus, in this manner there is provided a permanent fluid-tight connection between the diluent bag 9 and transfusion bag 4.

Figure 3:
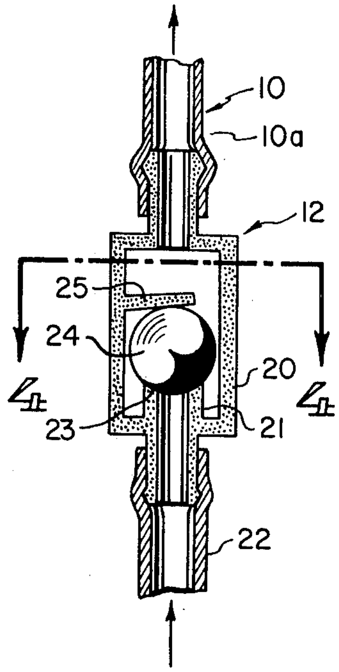
FIG. 3 is a cross-sectional view of a uni-directional flow fluid valve according to the present invention.
Figure 4:
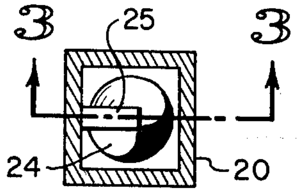
FIG. 4 is a cross-sectional view taken along the lines 4—4 of FIG. 3.

Referring to FIGS. 3 and 4, the uni-directional flow fluid valve 12 is provided with a housing 20. Interior of the housing 20 there is a cylindrical tubular structure 21. Tubular structure 21 is coupled to the hollow tubing 22 connecting the input of the valve member 12 to the diluent bag 9. At its upper end, the tubular structure 21 is formed with a curved valve seat 23 for receiving a spherical valve member 24. The valve member 24 is resiliently held in closed relationship relative to the valve seat 23 by means of a flexible rod-like member 25 which extends from the interior wall portion of the housing 20. The tubular member 10*a* attached to the transfusion bag 4 is fitted to the output end of the uni-directional flow fluid valve means 12.

The apparatus according to the present invention may be used in a number of ways. For example, a supply of diluent bags 9 may be kept in the operating room or other suitable location for use by a physician desiring to dilute packed red blood cells in a transfusion bag 4 which has been ordered from a blood service. Alternatively, an adequate supply of diluent bags 9 may be supplied with the transfusion bags 4, as ordered by a physician. In still another method, the diluent bag 9 may be pre-coupled to a transfusion bag 4 prior to its being delivered in response to an order from a physician. In any of the cases mentioned, when dilution of packed red blood cells is desired, a diluent bag 9, which is coupled to the transfusion bag 4 in the manner described above, is coupled so as to provide a permanent coupling between the diluent bag 9 and transfusion bag 4. When required and, if not previously done, the physician may simply and with one hand grasp the diluent bag 9 and squeeze vigorously. As the physician squeezes the diluent bag 9, the pressure causes the spherical valve member 24 to press against the spring member 25 in the uni-directional flow valve means 12. As the spherical valve member 24 is moved from the valve seat 23, fluid from the diluent bag 9 flows through the valve means 12 and the tubular member 10 and into the transfusion bag 4. Generally, the turbulence caused by the forced fluid flow into the transfusion bag 4 is sufficient to agitate the packed red blood cells to form a homogeneous mixture of diluent and red blood cells. The amount of diluent is premeasured and corresponds to the amount of plasma and other blood components removed from the red blood cells in the transfusion bag during the collection and processing of the blood.

Typically, the diluting fluid in the diluent bag 9 is either isotonic or slightly hypotonic so as not to cause hemolysis. Also it would not normally contain any calcium which could neutralize the effect of the anticoagulants and lead to clotting of the blood.

Since packed red blood cells diluted with the apparatus of the present invention and in the manner described can be made to have a viscosity which should be acceptable for rapid transfusions, it may be possible by means of the present invention to reduce, if not eliminate entirely, dependence on all commercial sources of whole blood. This is because the components available from present levels of volunteer donors is sufficient so long as the requirements for low-viscosity whole blood can be supplied by properly diluted packed red blood cells as described herein. It is apparent, that if the dependence on commercial blood sources can be reduced or eliminated, many of the problems involving hepatitis and other blood disorders associated with blood obtained from such sources will be reduced and, hopefully, eliminated. While a preferred embodiment of the invention has been described, it is contemplated that those skilled in the art may make various changes and modifications to the embodiment described without departing from the spirit and scope of the present invention. For example, a fitting such as fitting 11, described above with respect to FIG. 2, may be used at the free end of the tubular member 22 for insertion in the diluent bag 9 in the same manner as that used for the bag 4. In any event, appropriate fluid-tight seals are provided for sealing the various bags during storage and shipment. Accordingly, it is intended that the invention be not limited to the embodiment disclosed but rather that its scope be determined by reference to the claims and their equivalents hereinafter provided.

What is claimed is:

1. An apparatus for administering a diluent to a quantity of red blood cells contained in a transfusion blood container having an input port and an output port for transfusing a patient comprising:

a flexible, squeezable diluent bag for containing a diluent for red blood cells;

means for providing a permanent fluid-tight connection between said diluent bag and said input port of said transfusion blood container in a fluid-tight manner; and means forming a check valve means for preventing a back flow of fluid from said transfusion blood container to said diluent bag through said connecting means.

2. An apparatus according to claim 1 wherein the volume of the diluent bag is approximately 200 cc and the bag is sized and shaped for expressing substantially all of a fluid contained therein by one hand.

3. An apparatus for administering a diluent to a transfusion bag having at least one fitting receiving port comprising:

a flexible, squeezable diluent bag for containing a diluent suitable for diluting the contents of the transfusion bag;

a tubular member for transporting diluent from the diluent bag to the transfusion bag;

a fitting located at one end of the tubular member for permanently connecting the diluent bag to the fitting receiving port of the transfusion bag in a fluid-tight manner; and one-way valve means for preventing reverse fluid flow from the transfusion bag to the diluent bag.

4. An apparatus according to claim 3 wherein the fitting receiving port of the transfusion bag has a tubular member with an annular shoulder at the interior end thereof extending radially inwardly toward the axis thereof and the fitting comprises a shouldered portion for engaging the annular shoulder of the tubular member.

5. An apparatus according to claim 4 wherein the fitting comprises a generally conically-shaped member having an inwardly tapered surface extending from the exterior edge of the shouldered portion thereof and a centrally located fluid passageway in fluid communication with the tubular member.

6. A method of diluting the contents of a transfusion bag containing packed red blood cells comprising the steps of:

permanently attaching to the transfusion bag a flexible, squeezable diluent bag containing a premeasured amount of diluent suitable for diluting the red blood cells in the transfusion bag; and transferring the contents of the diluent bag to the transfusion bag to dilute the red blood cells contained therein while preventing a back flow of fluid from said transfusion bag to said diluent bag.

7. A method according to claim 6 wherein said step of transferring comprises the step of squeezing the contents of the diluent bag into the transfusion bag.

8. A method according to claim 6 wherein said step of attaching the diluent bag to a port of the transfusion bag comprises the step of permanently attaching the diluent bag to the transfusion bag by means of a fluid-tight tubular member and a fitting and said step of transferring the contents of the diluent bag to the transfusion bag while preventing a back flow of fluid therefrom comprises the step of squeezing the contents of the diluent bag into the transfusion bag through said fluid-tight tubular member, said fitting and a uni-directional flow fluid valve means.

* * * * *